(12) United States Patent
McEwen et al.

(10) Patent No.: US 8,048,105 B2
(45) Date of Patent: Nov. 1, 2011

(54) ADAPTIVE SURGICAL TOURNIQUET APPARATUS AND METHOD

(75) Inventors: James A. McEwen, Vancouver (CA); Michael Jameson, North Vancouver (CA); Michael A. Gebert, Vancouver (CA)

(73) Assignee: Western Clinical Engineering Ltd., Vancouver ( * ) Notice: Subject to any disclaimer, the term of this patent is extended or adjusted under 35 U.S.C. 154(b) by 368 days.

(21) Appl. No.: 11/737,258

(22) Filed: Apr. 19, 2007

(65) Prior Publication Data
US 2008/0262533 A1    Oct. 23, 2008

(51) Int. Cl.
*A61B 17/00* (2006.01)
(52) U.S. Cl. .................. 606/202; 606/201; 606/203
(58) Field of Classification Search .......... 606/201–203; 600/490–499; 601/149–152
See application file for complete search history.

(56) References Cited

U.S. PATENT DOCUMENTS

| | | | | |
|---|---|---|---|---|
| 3,552,383 | A | * | 1/1971 | Krueger et al. ............... 600/495 |
| 3,825,008 | A | * | 7/1974 | Shook .......................... 606/202 |
| 4,088,126 | A | * | 5/1978 | Gemind ........................ 600/490 |
| 4,294,261 | A | * | 10/1981 | Baker et al. ................... 600/504 |
| 4,321,929 | A | * | 3/1982 | Lemelson et al. ............. 600/301 |
| 4,469,099 | A | * | 9/1984 | McEwen ....................... 606/202 |
| 4,479,494 | A | * | 10/1984 | McEwen ....................... 606/202 |
| 4,520,819 | A | * | 6/1985 | Birmingham et al. ......... 606/202 |
| 4,520,820 | A | * | 6/1985 | Kitchin et al. ................. 606/202 |
| 4,548,198 | A | * | 10/1985 | Manes .......................... 606/202 |
| 4,635,635 | A | | 1/1987 | Robinette-Lehman |
| 4,671,290 | A | * | 6/1987 | Miller et al. .................. 600/494 |
| 4,677,984 | A | * | 7/1987 | Sramek ......................... 600/494 |
| 4,770,175 | A | * | 9/1988 | McEwen ....................... 606/203 |
| 4,796,184 | A | * | 1/1989 | Bahr et al. ..................... 600/492 |
| 5,048,536 | A | * | 9/1991 | McEwen ....................... 600/561 |
| 5,181,522 | A | * | 1/1993 | McEwen ....................... 600/561 |
| 5,254,087 | A | * | 10/1993 | McEwen ........................ 604/66 |
| 5,307,811 | A | * | 5/1994 | Sigwart et al. ................ 600/490 |
| 5,439,477 | A | * | 8/1995 | McEwen ....................... 606/203 |
| 5,454,831 | A | | 10/1995 | McEwen |
| 5,556,415 | A | * | 9/1996 | McEwen et al. .............. 606/202 |
| 5,569,304 | A | | 10/1996 | Ulrich |
| 5,649,954 | A | | 7/1997 | McEwen |
| 5,681,307 | A | | 10/1997 | McMahan |
| 5,741,295 | A | | 4/1998 | McEwen |

(Continued)

OTHER PUBLICATIONS

Office Action; Canadian IP Office; concerning CA 2514944; Jul. 8 2010; 3 pages.

*Primary Examiner* — Gary Jackson
*Assistant Examiner* — Erin Colello
(74) *Attorney, Agent, or Firm* — Hancock Hughey LLP

(57) ABSTRACT

An adaptive surgical tourniquet comprises: an inflatable cuff for encircling a limb of a patient; pressurizing means for pressurizing the cuff; pressure relief means for depressurizing the cuff; cuff pressure sensing means for sensing cuff pressure; limb occlusion pressure sensing means for sensing the patient's initial limb occlusion pressure at a selected time; physiologic characteristic sensing means for sensing a physiologic characteristic of the patient; and pressure regulator means for establishing an adapted limb occlusion pressure that is a predetermined function of the initial limb occlusion pressure and the physiologic characteristic, wherein the pressure regulator means is operable after the initial limb occlusion pressure is sensed for selectably activating the pressurizing means and the pressure relief means to maintain the cuff pressure above the adapted limb occlusion pressure for a time period suitably long for the performance of a surgical procedure.

4 Claims, 3 Drawing Sheets

U.S. PATENT DOCUMENTS

| | | | |
|---|---|---|---|
| 5,842,996 A * | 12/1998 | Gruenfeld et al. | 600/490 |
| 5,855,589 A * | 1/1999 | McEwen et al. | 606/202 |
| 6,051,016 A * | 4/2000 | Mesaros et al. | 606/202 |
| 6,248,083 B1 * | 6/2001 | Smith et al. | 600/585 |
| 6,299,629 B1 * | 10/2001 | Gruenfeld et al. | 606/202 |
| 6,589,267 B1 * | 7/2003 | Hui | 606/202 |
| 6,605,103 B2 * | 8/2003 | Hovanes et al. | 606/202 |
| 7,166,123 B2 * | 1/2007 | Hovanes et al. | 606/202 |
| 7,479,154 B2 * | 1/2009 | McEwen et al. | 606/202 |
| 7,485,131 B2 * | 2/2009 | Hovanes et al. | 606/202 |
| 2001/0041910 A1 | 11/2001 | McEwen | |
| 2006/0253150 A1 * | 11/2006 | McEwen et al. | 606/202 |
| 2009/0124912 A1 * | 5/2009 | McEwen et al. | 600/495 |

* cited by examiner

ADAPTIVE SURGICAL TOURNIQUET APPARATUS AND METHOD

FIELD OF THE INVENTION

This invention pertains to pneumatic tourniquet systems commonly used for stopping the flow of arterial blood into a portion of a surgical patient's limb to facilitate the performance of a surgical procedure, and for facilitating intravenous regional anesthesia. In particular, this invention pertains to pneumatic tourniquet apparatus for automatically adapting the pressure applied to a patient's limb by a tourniquet cuff as a function of changes in the patient's limb occlusion pressure during surgery.

BACKGROUND OF THE INVENTION

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes an inflatable portion, and the inflatable portion of the cuff is connected pneumatically through one or two cuff ports by flexible plastic tubing to a tourniquet instrument that includes a pressure regulator to maintain the pressure in the inflatable portion of the cuff, when applied to a patient's limb at a desired location, near a reference pressure that is above a minimum pressure required to stop arterial blood flow past the cuff during a time period suitably long for the performance of a surgical procedure. Many types of such pneumatic surgical tourniquet systems have been described in the prior art, such as those described by McEwen in U.S. Pat. Nos. 4,469,099, 4,479,494, 5,439,477 and by McEwen and Jameson in U.S. Pat. No. 5,556,415 and No. 5,855,589.

Many studies published in the medical literature have shown that the safest tourniquet pressure is the lowest pressure that will stop the flow of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible.

It is well established in the medical literature that the optimal guideline for setting the pressure of a constant-pressure tourniquet is based on "Limb Occlusion Pressure" (LOP). LOP can be defined as the minimum pressure required, at a specific time in a specific tourniquet cuff applied to a specific patient's limb at a specific location, to stop the flow of arterial blood into the limb distal to the cuff. The currently established guideline for setting tourniquet pressure based on LOP is that an additional safety margin of pressure is added to the measured LOP, to account for variations in physiologic characteristics and other changes that may be anticipated to occur normally over the duration of a surgical procedure.

Some surgical tourniquet systems of the prior art include means to measure LOP automatically. Prior-art tourniquet apparatus having automatic LOP measurement means are described by McEwen in U.S. Pat. No. 5,439,477 and by McEwen and Jameson in U.S. Pat. No. 5,556,415. Such prior-art systems have included blood flow transducers that employ a photoplethysmographic principle to sense blood flow in the distal limb, although other transducers have been suggested in the prior art to measure blood flow based on other principles. A blood flow transducer employing the photoplethysmographic principle uses light to indicate the volume of blood present in a transduced region, consisting of a combination of a residual blood volume and a changing blood volume resulting from arterial pulsations. An additional pressure margin based on recommendations in published surgical literature is added to the automatically measured LOP to provide a "Recommended Tourniquet Pressure" (RTP), as a guideline to help the surgical staff select the lowest tourniquet pressure that will safely stop arterial blood flow for the duration of a surgical procedure. Such prior-art systems allow the surgical staff to select the RTP, based on LOP, as the tourniquet pressure for that patient or to select another pressure based on the physician's discretion or the protocol at the institution where the surgery is being performed.

In U.S. Pat. App. No. 20060253150, McEwen and Jameson describe surgical tourniquet apparatus for automatically measuring LOP that overcomes many of the limitations of prior-art apparatus in four principal areas: safety, probability of successful LOP measurement, speed of LOP measurement, and accuracy of LOP measurement. The McEwen '150 apparatus does not introduce secondary hazards associated with the measurement of LOP, has a high probability of successful completion after LOP measurement is initiated, completes LOP measurement sufficiently fast so that the measurement of LOP does not disrupt or unduly delay normal activities in the operating room, and results in an LOP measurement that is accurate within surgically acceptable expectations so that it can be used as the basis for optimal setting of tourniquet pressure prior to inflation of the tourniquet cuff to facilitate surgery.

Despite the improved performance of the McEwen '150 apparatus in measuring LOP, there is one significant limitation: the apparatus does not measure or estimate any changes to LOP that may occur during surgery. Instead, the Recommended Tourniquet Pressure (RTP) equals the sum of the LOP measured prior to cuff inflation for surgery plus a pre-determined margin of safety. The margin of safety is set to be greater than the magnitude of any increase in LOP normally expected during surgery and may be dependent on the magnitude of the LOP, as described in McEwen '150. As a result, a constant RTP based on LOP measured prior to surgery may be higher than necessary to the extent that the magnitude of any increase in LOP during surgery is less than the magnitude of the predetermined margin of safety. Additionally, if LOP decreases during surgery below the LOP measured prior to surgery, then the RTP will be unnecessarily high by an even larger amount.

Several variables affecting LOP have been described in the prior art. Prior to surgery, LOP is affected by variables including the patient's limb characteristics (for example, limb shape, circumference and soft tissue characteristics at the cuff location), characteristics of the selected tourniquet cuff (for example, cuff design, cuff shape and cuff width), the technique of application of the cuff to the limb (for example, the degree of snugness or looseness and the absence, presence and type of underlying limb protection sleeve), physiologic characteristics of the patient including blood pressure and limb temperature, and other clinical factors (for example, the extent of any elevation of the limb during LOP measurement and the extent of any limb movement during measurement). After inflation of the tourniquet cuff to facilitate surgery, ongoing LOP during surgery is affected by variables including: the anesthetic technique employed (for example, whether a general or regional anesthetic is given, the types and dosages of anesthetic agents employed and the degree of attention paid to anesthetic management); the length of tourniquet time; isolation of the operative limb from systemic circulation; any change in limb position during surgery; and by any shift in the location of the cuff relative to the limb during surgery. Some but not all of these intraoperative variables change the LOP from the initial level of LOP measured before surgery by changing the patient's blood pressure, one of the variables affecting LOP.

The prior art describes a wide range of tourniquet apparatus for changing tourniquet pressure on the basis of a patient's intraoperative blood pressure. For example, in U.S. Pat. No. 4,479,494 McEwen describes pneumatic tourniquet apparatus in which pressure in a tourniquet cuff may be varied "adaptively" in response to changes in the patient's intraoperative systolic blood pressure. The apparatus of McEwen '494 selectably activates a pressurizing mechanism and a pressure relief mechanism to automatically maintain a substantially constant pressure difference between pressure in the tourniquet cuff and the patient's changing systolic blood pressure during surgery. McEwen '494 includes a tourniquet cuff having one cuff segment for occluding blood flow into the patient's limb and another cuff segment for sensing the patient's systolic blood pressure and includes recorder means for periodically recording the operational status of the apparatus. In addition to McEwen '494, others have described prior-art apparatus for setting or changing tourniquet pressure based on a patient's blood pressure, for example: Lemelson et al in U.S. Pat. No. 4,321,929; Miller et al in U.S. Pat. No. 4,671,290; Ulrich in U.S. Pat. No. 5,569,304; Gruenfeld et al in U.S. Pat. No. 5,842,996; and Hovanes et al in U.S. Pat. No. 6,605,103. However, such prior-art apparatus does not take into account many of the above-described variables that affect limb occlusion pressure and thus the tourniquet pressure is not optimal.

No apparatus known in the prior art adapts tourniquet pressure as a function of changes during surgery in a patient's limb occlusion pressure from an initial limb occlusion pressure. The present invention addresses the need for improved surgical tourniquet apparatus for automatically adapting the pressure applied to a patient's limb by a tourniquet cuff as a function of changes in the patient's limb occlusion pressure during surgery.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
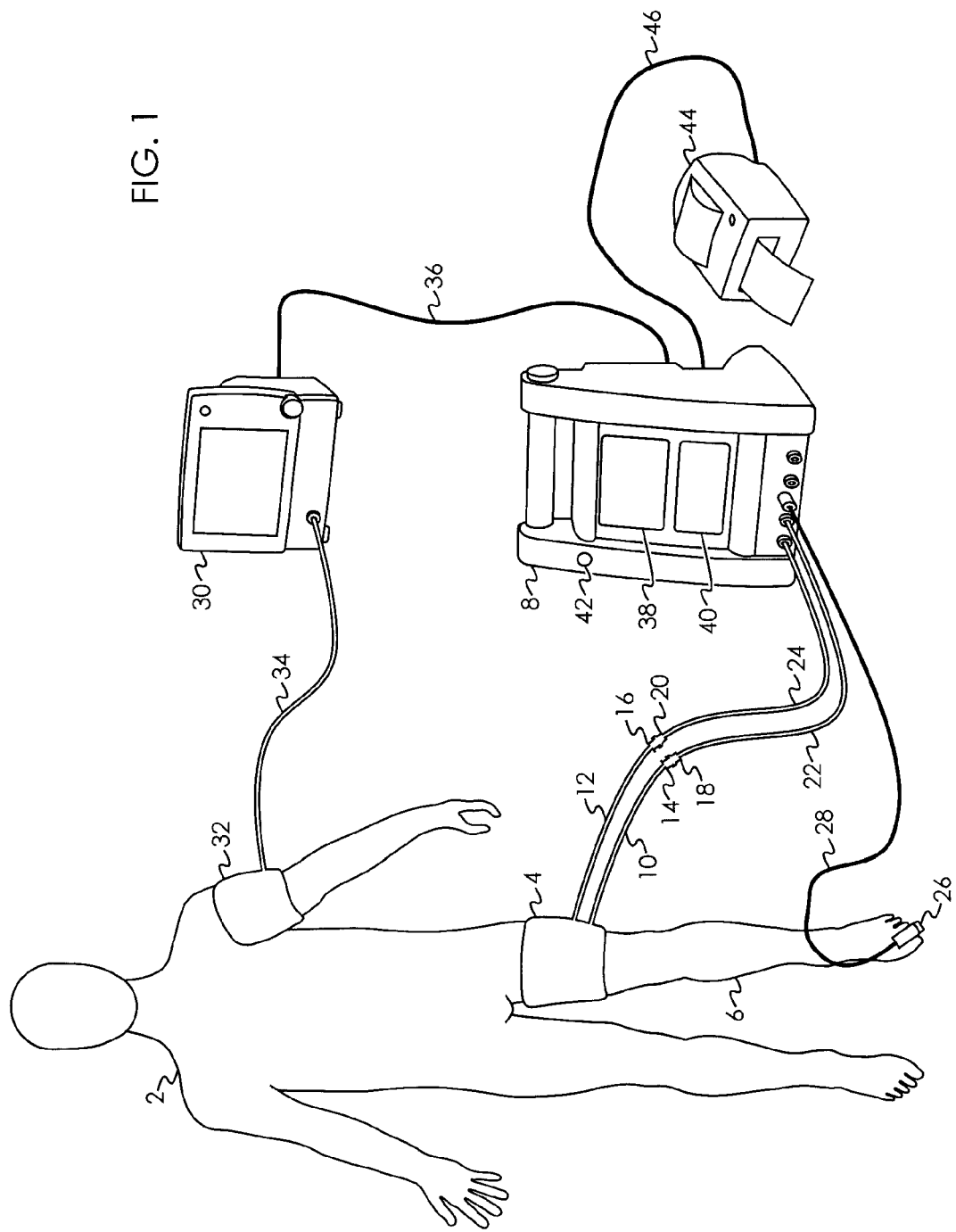
FIG. 1 is a pictorial representation of the preferred embodiment in a surgical application.

FIG. 1 shows the preferred embodiment with a patient 2 in a surgical application. Tourniquet cuff 4 is applied to encircle operative limb 6 of patient 2 and pneumatically connected to adaptive tourniquet instrument 8. The inflatable portion of pressurizing cuff 4 has two separate pneumatic connections and is generally similar in design and construction to the cuffs described by McEwen in U.S. Pat. Nos. 5,741,295, 5,649,954, 5,484,831 and by Robinette-Lehman in U.S. Pat. No. 4,635,635. Cuff 4 is a dual-port cuff, and separate pneumatic passageways to the inflatable portion of cuff 4 are provided by cuff port 10 and cuff port 12 so that each passageway is independent of the other. As shown in FIG. 1 cuff port 10 and cuff port 12 are of sufficient length to allow pneumatic connections to cuff 4 to be made outside of a sterile surgical field. Cuff port 10 and 12 are fitted with male locking connectors 14 and 16 (DSM2202, Colder Products Company, St. Paul, Minn.) respectively, and mate to form releasable pneumatic connections with female locking connectors 18 and 20 (PMC1704, Colder Products Company, St. Paul, Minn.). The connectors illustrated in FIG. 1 are shown connected and form part of the pneumatic passageways between instrument 8 and cuff 4. Pneumatic connections from instrument 8 to cuff 4 are made by flexible plastic tubing 22 and 24 which are fitted with female locking connectors 18 and 20 respectively.

Blood flow transducer 26 is applied to a digit of operative limb 6 and connected to adaptive tourniquet instrument 8 via multi-conductor shielded cable 28. Blood flow transducer 26 of the preferred embodiment employs the principle of photoplethysmography and is adapted for positioning on the limb distal to tourniquet cuff 4, although it will be appreciated that other types of blood flow transducers employing other principles may be used, and it will be appreciated that some types of blood flow transducers may be physically integrated into the structure of a tourniquet cuff. In the preferred embodiment, blood flow transducer 26 has a hinged plastic housing that is configured for application to a digit of a limb. Blood flow transducer 26 may be applied to a finger or thumb of the hand or a toe of the foot. Transducer 26 includes an infrared light source and photodetector positioned directly opposite each other such that light emitted by the light source is readily detected by the photodetector. As shown in FIG. 1 blood flow transducer 26 is positioned on operative limb 6 at a location that is distal to tourniquet cuff 4. This configuration permits blood flow transducer 26 to detect blood flow in operative limb 6 and changes in blood flow that occur in operative limb 6 as a result of the pressurization of cuff 4. Blood flow transducer 26 is used by adaptive tourniquet instrument 8 when performing the initial automatic measurement of limb occlusion pressure (LOP) prior to the commencement of surgery. LOP is the minimum pressure required, at a specific time in a specific tourniquet cuff applied to a specific patient's limb at a specific location, to stop the flow of arterial blood into the limb distal to the cuff. Instrument 8 operates as described in U.S. Pat. App. No. 20060253150, herein incorporated by reference, to initially measure limb occlusion pressure, the minimum pressure within cuff 4 at which blood flow is no longer detected by blood flow transducer 26.

During a surgical procedure that requires a regional or general form of anesthesia it is standard practice to monitor physiologic characteristics indicative of the physiologic status of the patient. Patient monitor 30 (Cardiocap/5, Datex-Ohmeda, Madison, Wis.) measures various physiologic characteristics of patient 2. These characteristics include blood pressure, oxygen saturation, heart rate, electrocardiogram, respiration rate, temperature and other characteristics of clinical interest. For clarity in FIG. 1 only the non-invasive blood pressure sensor of patient monitor 30, blood pressure cuff 32, is shown. Blood pressure cuff 32 is applied to a non-operative limb of patient 2 and connected to patient monitor 30 via pneumatic tubing 34. Patient monitor 30 uses the principle of oscillometry to non-invasively sense the blood pressure of patient 2 and determines values for systolic, mean, and diastolic arterial pressure. Patient monitor 30 is configured to automatically measure the blood pressure of patient 2 at three to five minute intervals; an operator may also manually initiate a non-invasive blood pressure measurement at any time. It will be apparent that patient monitor 30 could be adapted to sense the blood pressure of patient 2 in response to a signal from instrument 8. Alternatively, it will be apparent that blood pressure could be sensed continuously by means of an arterial pressure transducer or other continuous blood pressure monitoring means known in the art.

Patient monitor 30 includes a data communication interface. Monitor 30 is interrogated via this interface by instrument 8 as described further below to communicate the values of blood pressure and other physiologic characteristics measured by monitor 30 to instrument 8. Electrical cable 36 connects the data communication interface of patient monitor 30 to adaptive tourniquet instrument 8. In the preferred embodiment, electrical cables are used to conduct signals for communication between instrument 8 and patient monitor 30. It will be apparent to those skilled in the art that a wireless communication means could be used in place of electrical cables.

As shown in FIG. 1, instrument 8 has an operator interface consisting of graphic display panel 38, keypad 40, visual alarm indicator 42, and printer 44. Printer 44 is connected to instrument 8 via electrical cable 46.

Keypad 40 provides a means for an operator to control the operation of instrument 8. Keypad 40 includes keys which may be used by an operator to: start the measurement of Initial Limb Occlusion Pressure as described below; control the pressurization and depressurization of cuff 4; set and modify a tourniquet reference pressure level near which instrument 8 maintains the pressure of gas in cuff 4; set and modify alarm limits; select either a Constant Pressure Mode or Adaptive Pressure Mode of pressure regulation wherein instrument 8 either maintains the tourniquet reference pressure level at a constant value as selected by an operator or automatically adjusts the tourniquet reference pressure level in response to changes in Adapted Limb Occlusion Pressure as described further below; and to perform other functions.

Display panel 38 is employed for the selective display of alphanumeric information, including for example: Initial Limb Occlusion Pressure and Adapted Limb Occlusion Pressure values; tourniquet reference pressure level; cuff pressure; alarm reference "limits" or values; alphanumeric alarm messages describing detected alarm conditions; and other information required for the operation of instrument 8.

Figure 3:
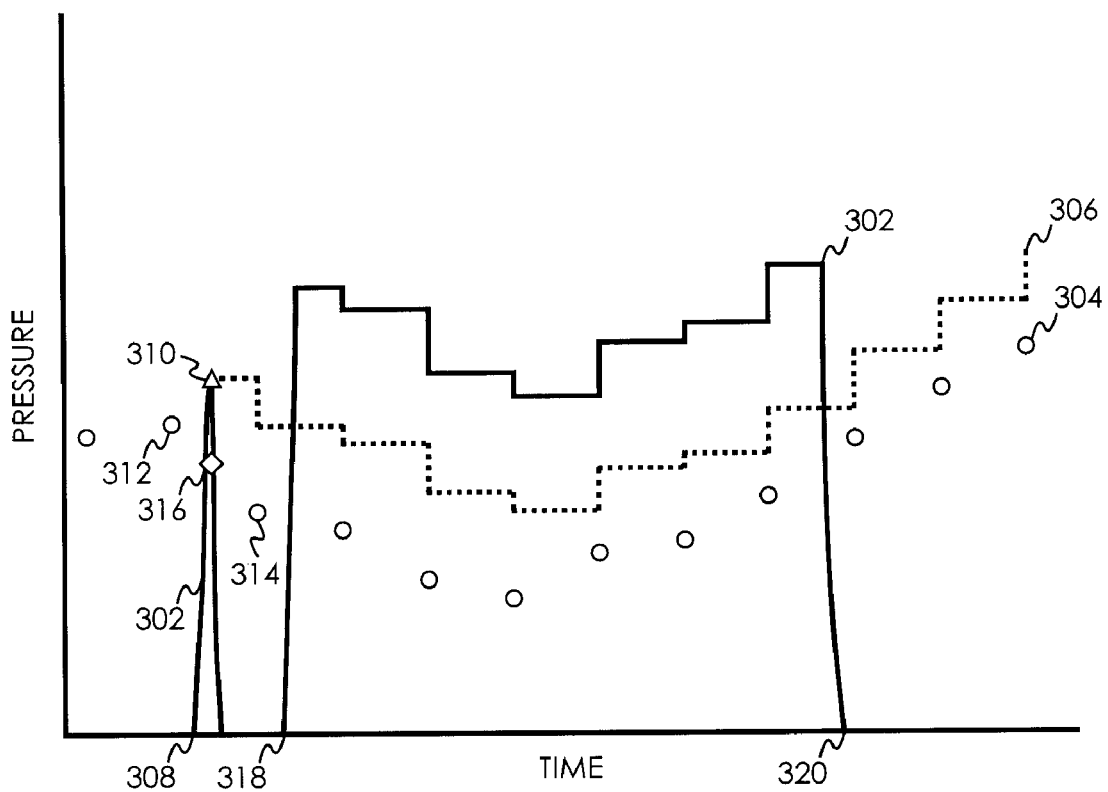
FIG. 3 is graphical representation of pressure values recorded by the preferred embodiment during a surgical procedure.

Printer 44 forms part of the operator interface of instrument 8 and produces a printed record of pressure values acquired and recorded by instrument 8 during a surgical procedure. An example of a typical printout is shown in FIG. 3 and described elsewhere below.

Visual alarm indictor 42 is a bright red light emitting diode (LED) which is activated by instrument 8 in response to detected alarm conditions. Instrument 8 also signals the presence of an alarm condition by generating an audible tone to further alert the operator to the presence of an alarm condition and displays alarm text messages describing the alarm condition on display panel 38. One example of a detected alarm condition that requires the operator's attention is a disconnection of electrical cable 36 that causes an interruption of communications with patient monitor 30.

Figure 2:
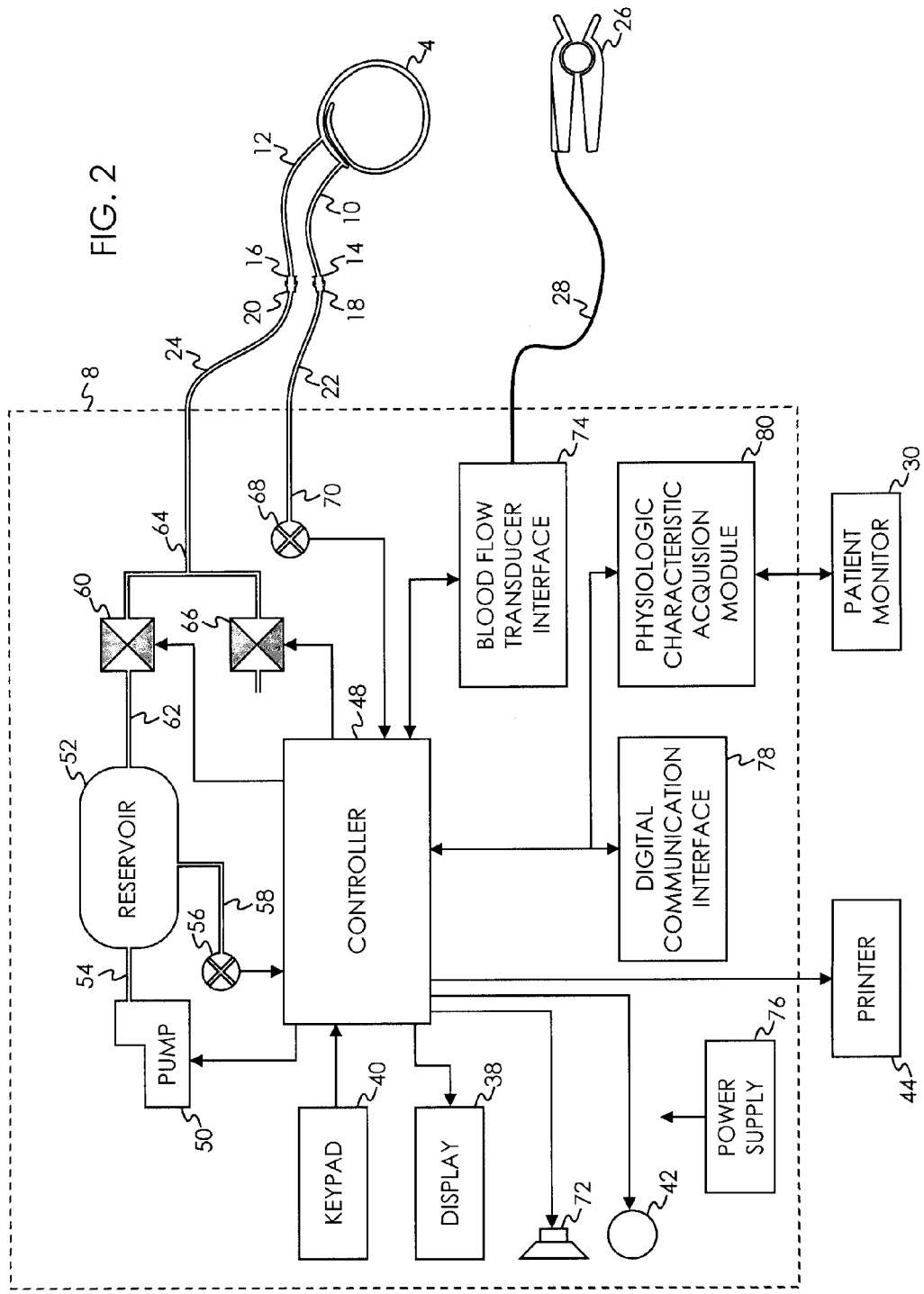
FIG. 2 is a block diagram of the preferred embodiment.

Referring now to the block diagram of instrument 8 shown in FIG. 2, controller 48 comprises a microcontroller (MC68HC16Z1, Freescale Semiconductor, Austin, Tex.), associated memory and control software, analog and digital peripheral interface circuitry, and other necessary support components.

Pneumatic pump 50 (KNF Neuberger, Inc., Trenton, N.J.) is pneumatically connected to reservoir 52 by tubing 54. In response to control signals from controller 48, pump 50 operates to pressurize reservoir 52. Reservoir pressure transducer 56 is pneumatically connected by tubing 58 to reservoir 52 and generates a reservoir pressure signal. The reservoir pressure signal is communicated to controller 48. Controller 48 acts to maintain the pressure in reservoir 52 near a reservoir pressure level. Controller 48 sets the reservoir pressure level to a pressure above the tourniquet reference pressure level, typically 100 mmHg above the tourniquet reference pressure level. In response to the reservoir pressure level and the reservoir pressure signal, controller 48 activates pump 50 to maintain the reservoir pressure near the reservoir pressure level.

Inflation valve 60 (EVO-3-12V, Clippard Instrument Laboratory, Cincinnati, Ohio) is configured as a two position normally closed valve. One side of the valve is pneumatically connected via tubing 62 to reservoir 52 the other side of the valve is connected to cuff 4 via the pneumatic passageway formed by manifold 64, tubing 24, connectors 20 and 16 and cuff port 12. When energized by controller 48, inflation valve 60 moves to the open position and allows pressurized gas to flow from reservoir 52 to cuff 4, thereby increasing the pressure of gas in the inflatable portion of cuff 4.

Deflation valve 66 (EVO-3-12V, Clippard Instrument Laboratory, Cincinnati, Ohio) is configured as a two position normally closed valve. One side of the valve is pneumatically connected to cuff 4 via the pneumatic passageway formed by manifold 64, tubing 24, connectors 20 and 16 and cuff port 10, the other side is open to atmosphere. When energized by controller 48, deflation valve 66 moves to the open position and allows pressurized gas to flow from cuff 4 to atmosphere, thereby decreasing the pressure of gas in the inflatable portion of cuff 4.

Cuff pressure transducer 68 is pneumatically connected to cuff 4 via the pneumatic passageway formed by tubing 70, tubing 22, connectors 18 and 14 and cuff port 10 and generates a cuff pressure signal which is communicated to controller 48. The separate independent pneumatic connection between the inflatable portion of cuff 4 and cuff pressure transducer 68 provides for an accurate indication of the actual pressure of gas within cuff 4 at any time.

Controller 48 operates to regulate the pressure of gas in cuff 4 near a tourniquet reference pressure level. The pressure regulator in the preferred embodiment operates as described in U.S. Pat. App. No. 20060253150 and is implemented as a control algorithm which selects opening times of valves 60 and 66 to maintain the pressure within cuff 4 near the tourniquet reference pressure level.

As noted above, controller 48 will, in response to generated alarm signals, alert the operator to an alarm condition by activating visual alarm indicator 42 and producing audible tones. Speaker 72 is connected to controller 48, and electrical signals having different frequencies to specify different alarm signals and conditions are produced by controller 48 and converted to audible sound by loudspeaker 72.

Blood flow transducer interface 74 comprises electronic circuitry that amplifies, filters, digitizes, and processes blood flow signals produced by blood flow transducer 26. Blood flow transducer interface 74 communicates signals representative of blood flow to controller 48.

Power supply 76 connects to an external AC supply and provides regulated DC power for the normal operation of all electronic components of instrument 8. Power supply 76 may also include a battery to enable instrument 8 to continue to operate in the absence of an external AC supply.

Digital communication interface 78 is electronic circuitry and software that permits instrument 8 to communicate with operating room information networks. When desired, controller 48 can operate to transmit pressure values recorded in memory to external data storage and display systems via digital communication interface 78. Controller 48 may also be configured to use digital communication interface 78 to obtain for patient 2 the values of physiologic characteristics sensed by other monitoring equipment in the operating room. Physiologic characteristics which are indicative of a change in limb occlusion pressure may be used by controller 48 as described below to estimate an Adapted Limb Occlusion Pressure value.

Physiologic characteristic acquisition module 80 is electronic circuitry and software that is configured for communicating with the data communication interface of patient monitor 30 to acquire values of monitored physiologic characteristics. Via physiologic characteristic acquisition module 80, controller 48 requests and receives the current values of physiologic characteristics sensed by patient monitor 30. These physiologic characteristics include blood pressure values resulting from periodic non-invasive or continuous blood pressure measurements, heart rate values, temperature values, and the values of other monitored physiologic characteristics.

Acquisition module 80 may also receive a real time blood pressure signal (waveform) from patient monitor 30 and calculate values of systolic, diastolic and mean blood pressure from this signal, thereby allowing controller 48 to more accurately determine the patient's blood pressure at or near the time that an initial limb occlusion pressure measurement is made. It will be appreciated that physiologic characteristic acquisition module 80 could be adapted to permit operation with other types of patient monitors, and that physiologic characteristic acquisition module 80 may be further adapted to communicate with other instruments through digital communication interface 78. It will also be appreciated that apparatus for the sensing of physiologic characteristics such as blood pressure and heart rate could readily be integrated into instrument 8.

Adapted Limb Occlusion Pressure

To automatically measure the Initial Limb Occlusion Pressure, controller 48 incrementally pressurizes cuff 4 and analyzes signals produced by blood flow transducer 26 as communicated by blood flow transducer interface 74. Controller 48 determines the minimum pressure required in cuff 4 to prevent arterial blood flow distal to the location of cuff 4; this minimum pressure is the Initial LOP. The Initial LOP takes into account the physiologic status of patient 2 at the time that limb occlusion pressure is measured. After the Initial LOP ($I_{LOP}$) has been determined, controller 48 acts to compute and automatically update an Adapted LOP value ($A_{LOP}$). In order to directly measure limb occlusion pressure, blood flow must be observed distal to cuff 4. The Adapted LOP value is an estimate of the limb occlusion pressure at a time when a direct measurement of limb occlusion pressure is not possible or safe, such as when cuff 4 is pressurized to prevent blood flow past cuff 4 for the duration of a surgical procedure. Various factors affect limb occlusion pressure. Some factors, such as the type of cuff and the location of the cuff on the limb to which it is applied, remain relatively constant for the duration of a surgical procedure. Other factors, such as arterial blood pressure, may vary widely during a surgical procedure. The Adapted LOP value computed by instrument 8 takes into account the effects on limb occlusion pressure of changes in blood pressure and other physiologic characteristics occurring after the time of direct limb occlusion pressure measurement. After the Initial LOP has been determined by controller 48, controller 48 queries physiologic characteristic acquisition module 80 for the blood pressure value and values of other physiologic characteristics measured near or at the time of the limb occlusion pressure measurement. The patient's blood pressure near or at the time of the limb occlusion pressure measurement is defined as the LOP Reference Blood Pressure ($BP_{LOPREF}$). Controller 48 uses the LOP Reference Blood Pressure in conjunction with the Initial LOP and blood pressure measurements taken subsequent to the determination of the Initial LOP to calculate the Adapted Limb Occlusion Pressure value. Controller 48 is configured to use either systolic or mean blood pressure values when calculating the Adapted LOP and may also use other physiologic characteristics such as heart rate in determining the current value of the Adapted LOP. In the preferred embodiment, the value of the Adapted LOP is equal to the sum of the Initial LOP and the difference of the current blood pressure value (BP) and the LOP Reference Blood Pressure value $\{A_{LOP}=I_{LOP}+(BP-BP_{LOPREF})\}$ Any inaccuracy in determining the value of the LOP Reference Blood Pressure is reflected in the value of the Adapted LOP. Because a patient's blood pressure can vary with time, it is desirable to obtain the result of a blood pressure measurement completed as near as is practical to the time that the Initial LOP is measured, so as to reduce uncertainty in the LOP Reference Blood Pressure and thereby increase the accuracy of the Adapted LOP. To obtain the value of a blood pressure measurement near the time that a limb occlusion pressure measurement is made, controller 48 may be configured to: automatically measure the Initial LOP near the time when a blood pressure measurement has been initiated by patient monitor 30; or use a selected value from a continuous blood pressure waveform. Alternatively, patient monitor 30 may be configured to begin a blood pressure measurement in response to control signals from instrument 8 near the time when a limb occlusion pressure measurement has been initiated.

Typically patient monitor 30 is configured to periodically sense blood pressure non-invasively at three to five minute intervals and controller 48 is configured to asynchronously initiate the measurement of limb occlusion pressure in response to operator input from keypad 40. New measured values for arterial blood pressure are therefore available at three to five minute time intervals for communication to physiologic characteristic acquisition module 80. To reduce uncertainty in the determination of the LOP Reference Blood Pressure, value controller 48 selects for use in the calculation of the LOP Reference Blood Pressure the values of blood pressure measurements obtained within a predetermined time window that overlaps a portion of, and preferably surrounds, the time period which the limb occlusion pressure measurement is completed. In the preferred embodiment, the predetermined time window is 6 minutes before and 6 minutes after the time that a measurement of Initial LOP is completed. Controller 48 computes the LOP Reference Blood Pressure from blood pressure measurements that occur within the predetermined time window using a time weighted averaging function, the greatest weight being given to the blood pressure measurement that occurs closest in time to the measurement of Initial LOP. It will be apparent that other functions may be used to calculate the LOP Reference Blood Pressure and that the duration of the predetermined time window may be modified. It will also be apparent that if patient monitor 30 is configured to continuously measure blood pressure or synchronously measure blood pressure at a time when limb occlusion pressure is being measured, the predetermined time window could be reduced and interpolation may not be required by controller 48 in calculating the LOP Reference Blood Pressure.

When cuff 4 has been pressurized to occlude blood flow in limb 6 for the duration of a surgical procedure, instrument 8 may be configured by an operator through keypad 40 to function in either a "Constant Pressure Mode" or an "Adaptive Pressure Mode" of operation. In the Constant Pressure Mode of operation, controller 48 maintains the tourniquet reference pressure level at a constant pressure level selected by an operator of instrument 8, while continuing to compute and display an Adapted LOP value. In the Adaptive Pressure Mode of operation, controller 48 automatically sets the tourniquet reference pressure level to a level proportional to the Adapted LOP value computed by controller 48. Adapting the tourniquet reference pressure level to changes in limb occlusion pressure helps to maintain the lowest, safest pressure within cuff 4 that prevents the flow of arterial blood into the limb distal to cuff 4 for the duration of the surgical procedure.

Controller 48 sets the tourniquet reference pressure level to a level that is a function of the value of the Adapted LOP. In the preferred embodiment, the tourniquet reference pressure ($T_{REF}$) level equals the sum of 1.2 times the Adaptive LOP value and 20 mmHg $\{T_{REF}=1.2A_{LOP}+20\}$ This relationship between Adapted LOP and tourniquet reference pressure level has been chosen to provide a linear approximation of recommendations appearing in the surgical literature for selecting a recommended tourniquet cuff pressure based on limb occlusion pressure. It will be appreciated that other mathematical relationships may be used to set the tourniquet reference pressure level as a function of the value of Adapted LOP.

If while operating in Adaptive Pressure Mode controller 48 detects an alarm condition that indicates an Adapted LOP value cannot be calculated, for example in the event of patient monitor 30 being unable to complete a blood pressure measurement within a predetermined time window, controller 48 will begin operation in the Constant Pressure Mode and will maintain the tourniquet reference pressure level at its current level. The operator of instrument 8 will be alerted to the alarm condition and the change in operating mode via display panel 38, alarm indicator 42 and speaker 72.

Controller 48 maintains in memory a pressure history register and acts to periodically record within this register the current values of: cuff pressure as indicated by cuff pressure transducer 68; tourniquet reference pressure levels as set by the operator or automatically by controller 48; blood pressure as measured by patient monitor 30; Initial Limb Occlusion Pressure; LOP Reference Blood Pressure; and Adapted LOP as computed by controller 48. The frequency at which controller 48 records pressure values in the pressure history register is dependent upon the type of pressure value. For example, blood pressure values are recorded each time a blood pressure measurement has been completed by patient monitor 30; cuff pressure values are recorded at predetermined intervals of 40 ms; and the Initial LOP is recorded when a limb occlusion pressure measurement has been completed. The pressure history register maintained by controller 48 maintains the temporal relationship between recorded values. Controller 48 can act to communicate the contents of the pressure history register to printer 44 to provide the operator with a printed record of the pressures values; the printed record may be tabular or graphical as shown in FIG. 3. Controller 48 can also communicate the contents of the pressure history register to digital communication interface 78 so that the information can be made available to operating room information networks.

Typical Use in Surgery

To enable a better understanding of the preferred embodiment, its typical use in a surgical procedure is described below.

An operator first applies blood pressure cuff 32 to a non-operative limb of the patient and configures patient monitor 30 to automatically sense physiologic characteristics including blood pressure at regular intervals.

The operator then selects an appropriately sized cuff 4 for application to the operative limb 6 of the patient and secures cuff 4 around patient limb 6. Pneumatic passageways from instrument 8 to the inflatable portion of cuff 4 are completed by mating connectors 16 and 20, and connectors 14 and 18. Many different sizes and shapes of cuff 4 may be optionally used with instrument 8 to accommodate different physical sizes of patients and patient limbs. Cuffs may vary in length, width, shape, and application technique; also some cuffs may be applied with a soft limb protection sleeve located between the limb and the cuff. The specific level of pressure required in tourniquet cuff 4 to stop blood flow past cuff 4 at a particular time is affected by variables including the characteristics of cuff 4 and any underlying sleeve, the technique used in applying cuff 4, the physical characteristics of limb 6 at the location where cuff 4 is applied, and the physiological characteristics of the patient, including blood pressure. Many of the variables that affect the initial measured limb occlusion pressure remain unchanged throughout a surgical procedure; blood pressure is one physiologic characteristic that has been shown to vary substantially over time and thus has a substantial influence on limb occlusion pressure during surgery.

Accordingly, to maintain the tourniquet cuff pressure at the lowest and safest level throughout surgery, the operator of instrument 8 may choose to initiate a measurement of Initial LOP and to operate instrument 8 in Adaptive Pressure Mode.

To perform a rapid and accurate measurement of Initial LOP, the operator first applies blood flow transducer 26 to a digit of patient limb 6 distal to the position of cuff 4. The operator then initiates the measurement of Initial LOP by activating a key on keypad 40. Instrument 8 then completes the measurement within 20-40 seconds by automatically increasing the pressure in cuff 4 to a pressure at which arterial blood flow pulsations are no longer detected by blood flow transducer 26. At this time, instrument 8 determines the Initial LOP and the LOP Reference Blood Pressure, which is the patient's blood pressure nearest to the time at which the Initial LOP is determined. As described above, instrument 8 computes an Adapted LOP using the Initial LOP, LOP Reference Blood Pressure and subsequent blood pressure measurements made by patient monitor 30.

When cuff 4 is pressurized for the duration of a surgical procedure and the Adaptive Pressure Mode of operation has been selected, controller 48 operates inflation valve 60 and deflation valve 66 to regulate the pressure in cuff 4 at a level above and proportional to the Adapted LOP value.

The Adapted LOP value is adapted by instrument 8 to reflect changes in the patient's limb occlusion pressure as a result of changes in blood pressure throughout the duration of the surgical procedure. To improve the responsiveness of the adaptation when blood pressure is measured periodically, controller 48 can be configured to use other monitored physiologic characteristics to estimate the Adapted LOP. For example, an increase in heart rate may be indicative of an increase in blood pressure, and controller 48 may therefore increase the Adaptive LOP value by a predetermined amount in response to a predetermined increase in heart rate, thereby helping to assure that blood will be prevented from flowing distal to cuff 4 in such a situation. When in Adaptive Pressure Mode, instrument 8 acts to maintain the pressure in cuff 4 at the lowest safe level throughout the surgical procedure. In the event of a predetermined alarm condition, such as loss of communication with patient monitor 30, controller 48 alerts the operator by displaying a text message on display panel 38, activating alarm light 42, and generating an audio tone via speaker 72. Controller 48 also reverts to Constant Pressure Mode and maintains the tourniquet reference pressure at its current level if an Adaptive LOP value cannot be computed due to the absence of physiologic characteristic data from patient monitor 30.

At the conclusion of the surgical procedure or at any other time, an operator may, via keypad 40, direct controller 48 to produce a printout of pressure values that were recorded in the pressure history register maintained by controller 48. An example of a printout from printer 44 is depicted in FIG. 3. In this example, pressure values are plotted against time on a graph. The values of cuff pressure are represented by the solid line 302; the values of measured blood pressure are represented by circle symbols 304; and values of Adapted LOP are represented by the dashed line 306. As can be seen in FIG. 3, cuff 4 is initially briefly pressurized (308) to measure limb occlusion pressure; the value of the Initial Limb Occlusion Pressure is represented by the triangle symbol 310 on the graph. The values of blood pressure measurements labeled 312 and 314 that immediately precede and follow the limb occlusion pressure measurement occur within the predetermined window of time described above and are used by controller 48 to determine the value of the LOP Reference Blood Pressure. The LOP Reference Blood Pressure is represented by the diamond symbol 316 on the graph. As can be seen in FIG. 3, the value of the LOP Reference Blood Pressure 316 is established near the time that the Initial LOP 310 is determined. Values of Adapted LOP 306 are computed after the Initial LOP 310 and LOP Reference Blood Pressure 316 have been determined. At the start of the surgical procedure, cuff 4 is pressurized (318). During the procedure the pressure level in cuff 4 is maintained above the Adapted LOP value 306 as described above to prevent blood flow distal to cuff 4. As can be seen in FIG. 3, the pressure within cuff 4 varies in relation to changes in the value of the Adapted LOP. At the completion of the procedure (320), cuff 4 is depressurized and should normally be removed from the operative limb.

We claim:

1. An adaptive surgical tourniquet, comprising:
    an inflatable cuff for encircling a limb of a patient;
    pressurizing means for pressurizing the cuff;
    pressure relief means for depressurizing the cuff;
    cuff pressure sensing means for sensing cuff pressure;
    limb occlusion pressure sensing means for sensing the patient's initial limb occlusion pressure at a selected time;
    physiologic characteristic sensing means for sensing blood pressure of the patient; and
    pressure regulator means operable after the initial limb occlusion pressure is sensed for selectably activating the pressurizing means and the pressure relief means to maintain the cuff pressure above an adapted limb occlusion pressure for a time period suitably long for the performance of a surgical procedure;
    wherein the physiologic characteristic sensing means further senses a second physiologic characteristic of the patient, and wherein the pressure regulator means further establishes the adapted limb occlusion pressure to be a predetermined function of the initial limb occlusion pressure, the blood pressure and the second physiologic characteristic.

2. The adaptive surgical tourniquet as defined in claim 1 wherein the limb occlusion pressure sensing means senses the patient's initial limb occlusion pressure by measuring arterial pulsations of blood flow in the limb distal to the cuff, by increasing the cuff pressure from a level near zero to a lowest level at the selected time when the arterial pulsations have a magnitude less than a minimum detection threshold, by producing the initial limb occlusion pressure to be indicative of the lowest level, and by decreasing the cuff pressure upon production of the initial limb occlusion pressure.

3. The adaptive surgical tourniquet as defined in claim 1, wherein the pressure regulator means further maintains the cuff pressure near a tourniquet pressure level having a predetermined relationship to the adapted limb occlusion pressure.

4. The adaptive surgical tourniquet as defined in claim 1, wherein the pressure regulator means further maintains the cuff pressure near a tourniquet pressure level equal to the sum of a first predetermined pressure level plus a second pressure level proportional to the value of the adapted limb occlusion pressure.

* * * * *